(12) United States Patent
Streeter

(10) Patent No.: US 10,456,567 B2
(45) Date of Patent: Oct. 29, 2019

(54) TOPICAL COOLED DERMAL DEVICE

(71) Applicant: L'OREAL, Paris (FR)

(72) Inventor: John Streeter, Redmond, WA (US)

(73) Assignee: L'OREAL, Paris (FR)

( * ) Notice: Subject to any disclaimer, the term of this patent is extended or adjusted under 35 U.S.C. 154(b) by 30 days.

(21) Appl. No.: 15/198,371

(22) Filed: Jun. 30, 2016

(65) Prior Publication Data

US 2018/0001069 A1    Jan. 4, 2018

(51) Int. Cl.
| | |
|---|---|
| *A61M 35/00* | (2006.01) |
| *A61N 1/04* | (2006.01) |
| *A61N 1/32* | (2006.01) |
| *A61N 1/40* | (2006.01) |

(52) U.S. Cl.
CPC ............ *A61M 35/00* (2013.01); *A61N 1/04* (2013.01); *A61N 1/0404* (2013.01); *A61N 1/328* (2013.01); *A61M 35/003* (2013.01); *A61M 2205/054* (2013.01); *A61M 2205/3606* (2013.01); *A61N 1/0412* (2013.01); *A61N 1/327* (2013.01); *A61N 1/40* (2013.01)

(58) Field of Classification Search
CPC .... A61M 35/00; A61M 35/003; A61M 37/00; A61M 2037/0007; A61M 2205/054; A61M 2205/3606; A61M 35/20; A61N 1/04; A61N 1/0404; A61N 1/0412; A61N 1/0428; A61N 1/0476; A61N 1/18; A61N 1/30; A61N 1/303; A61N 1/325; A61N 1/327; A61N 1/328; A61N 1/40
See application file for complete search history.

(56) References Cited

U.S. PATENT DOCUMENTS

| | | | |
|---|---|---|---|
| 6,251,100 B1 * | 6/2001 | Flock | A61B 5/411 604/20 |
| 6,743,211 B1 * | 6/2004 | Prausnitz | A61B 5/14514 424/449 |
| 7,549,987 B2 * | 6/2009 | Shadduck | A61B 18/04 606/28 |

* cited by examiner

*Primary Examiner* — Shefali D Patel
(74) *Attorney, Agent, or Firm* — Oblon, McClelland, Maier & Neustadt, L.L.P.

(57) ABSTRACT

A dermal device for skincare therapy is provided including: a fluid circuit including a fluid pump and a reservoir; and a dermal interface configured to contact a user's skin, the dermal interface including at least one electrode and part of the fluid circuit having at least one perforation, wherein the at least one electrode is configured to deliver an energy pulse to the contacted skin, wherein the reservoir is configured to hold at least one topical, wherein the fluid pump is configured to pump the at least one topical through the fluid circuit and extrude the at least one topical through the dermal interface.

13 Claims, 6 Drawing Sheets

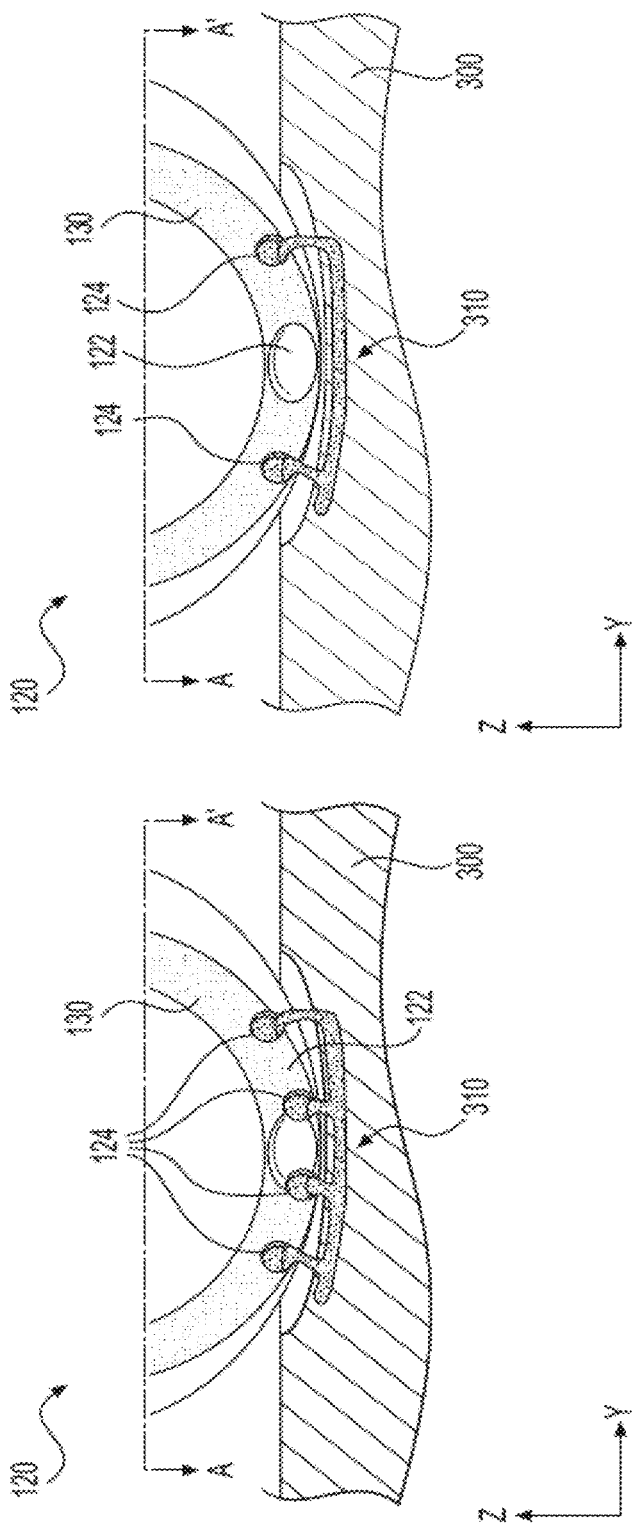

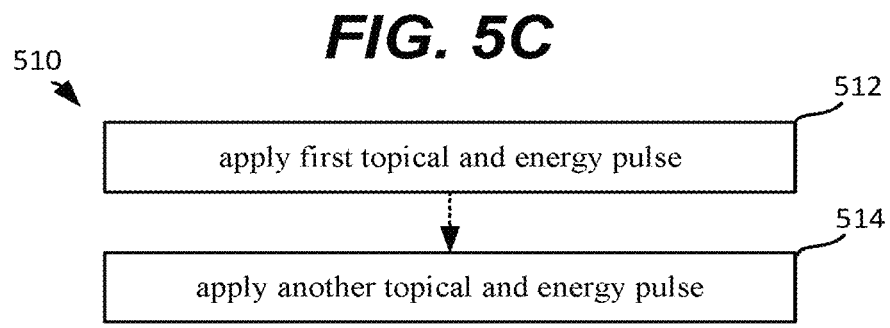
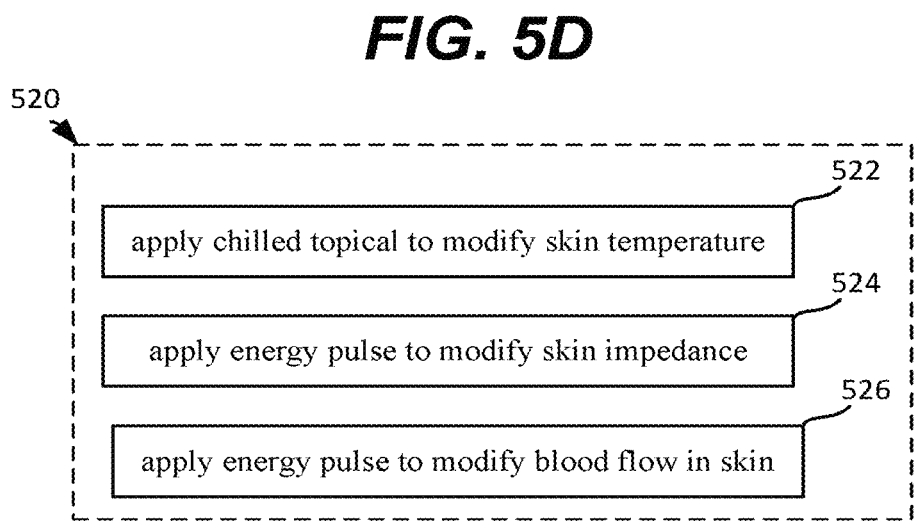
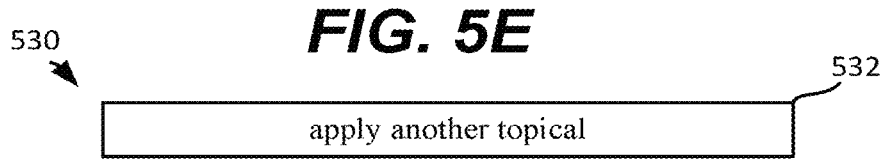

TOPICAL COOLED DERMAL DEVICE

BACKGROUND

Field

The present application is directed to a device and method for enhancing radiofrequency energy therapy to select layers of a user's skin.

SUMMARY

In an embodiment, a dermal device for skincare therapy is provided including: a fluid circuit including a fluid pump and a reservoir; and a dermal interface configured to contact a user's skin, the dermal interface including at least one electrode and part of the fluid circuit having at least one perforation, wherein the electrode(s) is configured to deliver an energy pulse to the contacted skin, wherein the reservoir is configured to hold at least one topical, wherein the fluid pump is configured to pump the least one topical through the fluid circuit and extrude the topical through the dermal interface.

In an embodiment, the perforation is configured to surround the electrode interfacing the skin.

In an embodiment, an energy pulse is applied to the skin configured to reduce a skin impedance, wherein the contacted skin is conditioned for the skincare therapy by a reduction in the skin impedance.

In an embodiment, the topical is chilled, wherein the contacted skin is conditioned for the skincare therapy by a reduction in temperature.

In an embodiment, the dermal interface is configured to be removable.

In an embodiment, the dermal device further includes a power source to generate the energy pulse.

In an embodiment, a method for conditioning a user's skin is provided including: conditioning the skin for an energy pulse; applying a chilled topical and the energy pulse to the skin; and conditioning the skin after the energy pulse.

In an embodiment, conditioning the skin for an energy pulse includes applying a chilled topical configured to modify a temperature of the skin.

In an embodiment, conditioning the skin for an energy pulse includes applying an energy pulse configured to modify an impedance of the skin.

In an embodiment, conditioning the skin for an energy pulse includes applying an energy pulse configured to modify a blood flow in the skin.

In an embodiment, applying a chilled topical and the energy pulse to the skin includes applying a first topical and energy pulse, and applying another topical and energy pulse.

In an embodiment, conditioning the skin after the energy pulse includes applying another topical.

BRIEF DESCRIPTION OF THE DRAWINGS

A more complete appreciation of the embodiments and many of the attendant advantages thereof will be readily obtained as the same becomes better understood by reference to the following detailed description when considered in connection with the accompanying drawings, wherein:

FIGS. 3A-3B are drawings of a side view in an z-y plane of a dermal interface contacting the skin and applying a topical to the skin according to an example;

FIG. 5C shows examples of applying a chilled topical and the energy pulse to the skin;

FIG. 5D shows examples of conditioning the skin prior to the energy pulse;

FIG. 5E shows examples of conditioning the skin after the energy pulse;

DETAILED DESCRIPTION

Figure 1A:
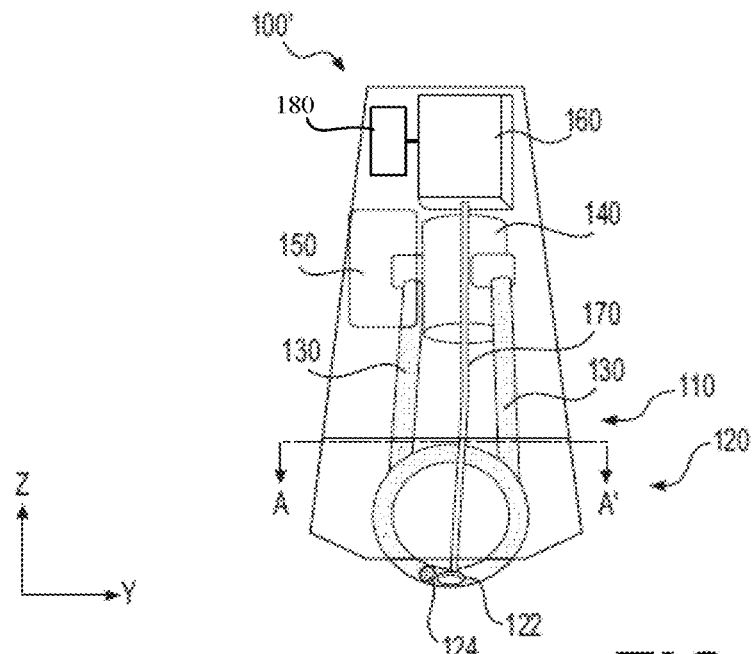
FIG. 1A is a drawing of a side view in an z-y plane of a dermal device for skincare therapy having a dermal interface configured to be in contact with a user's skin according to an example.

A dermal device is presented to enhance Radiofrequency (RF) energy therapy to a user's skin. RF energy therapy may be used to promote at least one of neocollagenesis, neoelastogenesis, and deposition of new hyaluronic acid within a layer of the skin or tissue. RF energy therapy uses an energy pulse that may heat tissue in order to achieve its therapeutic effect. Alternatively, the tissue can be heated as a side effect from the energy pulse. The energy pulse results in a penetration depth into the skin that can be based on and/or limited by a safety tolerance of one or more layers of the skin or tissue.

In an aspect, the energy pulse can be pulsed at a frequency, pulse width, and amplitude for a duration in order to provide the therapeutic effect. A topical can be used to condition the skin in conjunction with the energy pulse. Examples of the topical can include a therapeutic or conditioning agent such as a toner (e.g. L'Oreal Paris Hydrafresh), a skin cleanser (e.g. Clarisonic Sonic Radiance), and a serum (e.g. L'Oreal Paris Revitalift), as well as any other applicable formulation for conditioning skin.

The topical can serve multiple purposes in conditioning the skin and enhancing the RF energy therapy including protecting the skin from the side effects of the energy pulse, providing hydration and cooling for the skin/electrode interface, reducing impedance of the skin/electrode interface, reducing the skin surface temperature, as well as providing beneficial actives for recovery of one or more layers of skin after application of the energy pulse.

Optionally, more than one topical can be circulated in coordination with the energy pulse. For example, a first topical can be circulated prior to activation of the energy pulse, a second topical can be circulated during activation of the energy pulse, and a third topical can be circulated after activation of the energy pulse.

A dermal device is presented that can enhance the RF energy therapy by conditioning the skin and/or the topical. In one example, while providing the energy pulse, the dermal device can be configured to apply cooling and/or a cooled topical to the skin and to modify a safety tolerance of one or more layers of the skin. Modification of the safety tolerance can allow for a modified penetration depth of the energy pulse into the skin. Additionally, use of a cooled topical in a coordinated manner may increase efficiency and efficacy of the RF energy therapy, as well as mitigate or reduce a side effect.

In an example, conditioning of the skin can be done simultaneously or in synchrony with an aspect of the energy pulse including an energy pulse frequency, pulse width, and/or amplitude. An example of the energy pulse frequency for dermal RF energy therapy can be on an order of 1 MHz frequency with power ranging from 5-8 W. In another example, the conditioning of the skin can be done simultaneously or in synchrony based on an aspect of the user's skin including a heat capacity rate of one or more layers of the skin, an impedance of the skin, a hydration level of the skin or any other aspect of the user's skin.

Use of the dermal device can add an improved level of device safety and efficacy in RF energy therapy or other energy based therapies. A synergistic combination of the dermal device and a topical may be packaged and marketed together.

Referring now to the drawings, wherein like reference numerals designate identical or corresponding parts throughout the several views.

FIGS. 1A-B

FIG. 1A is a drawing of a side view in a z-y plane of a dermal device 100' for skincare therapy according to an example. The dermal device 100' can include a body section 110 and a dermal interface 120. The dermal interface 120 can be configured to be removable from the body section 110 such that a different dermal interface can be interchanged.

The body section 110 can include an user interface 180, an energy source 160 and a fluid circuit 130 connecting a fluid pump 140, a reservoir 150, and a portion configured to connect to the dermal interface 120. The reservoir 150 is configured to hold and to chill at least one topical. In an example, the reservoir 150 can include a Peltier cooling system for chilling. The fluid pump 140 is configured to pump the topical through the fluid circuit 130. In an example, the fluid pump 140 can be configured to pump at a set of topicals through the fluid circuit 130 in coordination with the energy source 160 (see FIG. 5). In an example, the user interface 180 can have a display and a set of buttons (not shown) for a user input. The user input can include one or more control operations for using the dermal device 100 including a start operation, a duration, an intensity of the energy pulse, a temperature of the cooled topical, a timing of synchronization of applying the cooled topical and powering the energy pulse, and identifying a dermal interface 120 and a topical.

Figure 1B:
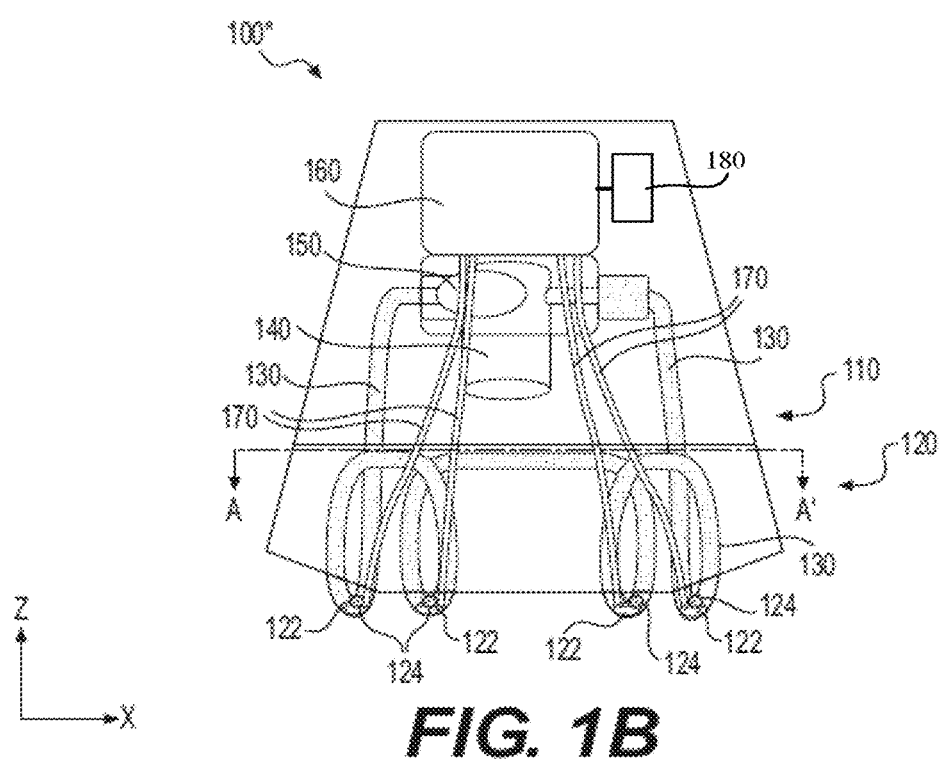
FIG. 1B is a drawing of a side view in an z-x plane of the dermal device having an alternate dermal interface according to an example.

The dermal interface 120 can include at least one electrode 122 and part of the fluid circuit 130 having one or more perforations 124. The energy source 160 is in communication with the electrode(s) 122 using one or more electrical connections 170 and is configured to produce the energy pulse. In an aspect, the dermal device 100 can have a set of dermal interfaces where each dermal interface can be configured to have a unique electrode configuration resulting in a unique spatial current density or power density to be applied to the skin. As shown in FIG. 1B, a dermal device 100'' can include a dermal interface 120 having an extended fluid circuit 130 with a distributed set of electrodes 122 and the set of perforations 124. An electrode configuration is preferably configured to limit the power density to not exceed 1 W/cm$^2$.

The energy source 160 can include a battery or a connection to another power source such as a wall plug. At least one of the user interface 180, the energy source 160 and the fluid pump 140 can further include circuitry configured to synchronize their activity, such as shown in FIG. 5.

A set of perforations 124 can be configured to extrude a topical 310 at the skin interface, providing a cooling effect to the skin (See FIGS. 3A and 3B). In an aspect each perforation 124 is preferably located such that the topical 310 is extruded prior to the electrode 122 contacting the skin. In an example, a set of perforations 124 can be configured to surround each electrode 122 such that the dermal device can be moved in any direction. In another example, an elongated perforation 126 can be configured to surround each electrode 122 such that the dermal device can be moved in any direction (See FIG. 2B). Alternatively, the set of perforations 124 can be adjacent to each electrode 122 according to an example (See FIGS. 2A, 3B).

In an aspect, the fluid pump 140 can be configured to pump the topical 310 through the fluid circuit 130 based on activation of the energy source 160. For example, when the energy source 160 changes the energy pulse frequency, pulse width, and/or amplitude, the conditioning required of the skin may change as well. In an aspect, the energy pulse can be configured to condition the skin by applying a potential in order to modify impedance of the skin prior or during the RF energy therapy.

FIG. 2A

Figure 2A:
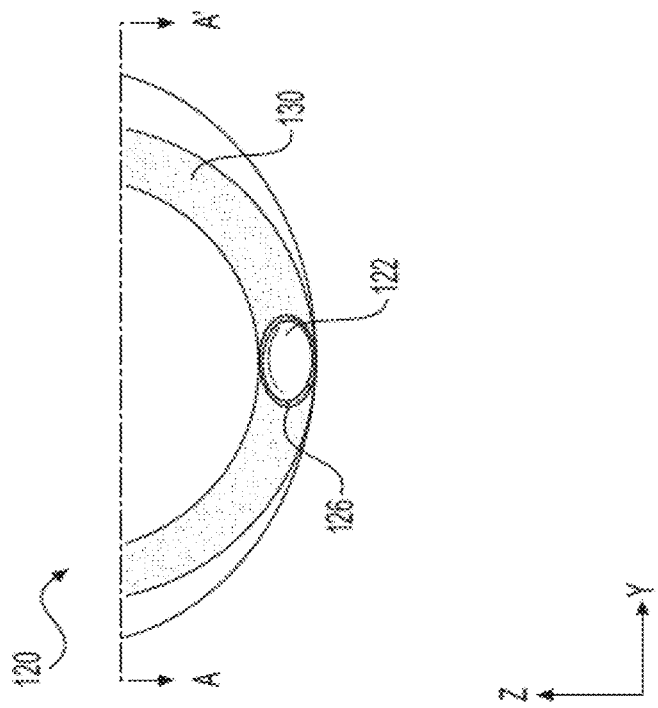
FIG. 2A is a drawing of a side view in an z-y plane of a dermal interface having a set of perforations and two electrodes configured to deliver an energy pulse to the contacted skin according to an example.
Figure 2B:
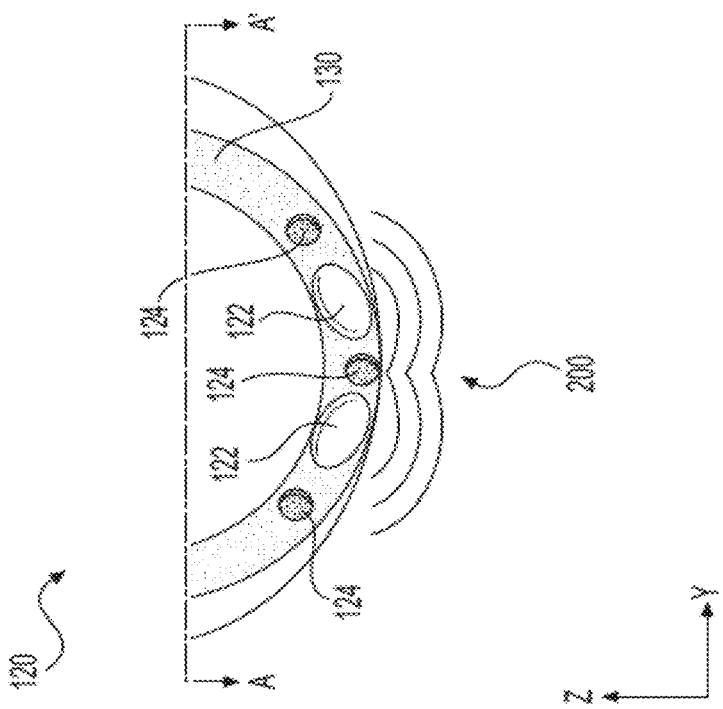
FIG. 2B is a drawing of a side view in an z-y plane of a dermal interface having an elongated perforation surrounding an electrodes according to an example.

FIG. 2A is a drawing of a side view in a z-y plane of a dermal interface 120 having a set of perforations 124 and two electrodes 122 producing an energy pulse 200 according to an example. The energy pulse can be either monopolar or bipolar. In an example, a monopolar configuration can utilize a return electrode in a handle (not shown) of the dermal device. However, an energy pulse 200 with a set of electrodes 122 in a bipolar configuration is preferred (See FIG. 2A).

FIGS. 3A-B

FIG. 3A is a drawing of a side view in a z-y plane of a dermal interface 120 having multiple perforations 124 and interfacing with the skin 300 while applying the topical 310 according to an example. FIG. 3B is a drawing of a side view in a z-y plane of a dermal interface 120 having a pair of perforations 124 and interfacing with the skin 300 while applying the topical 310 according to an example.

FIG. 4

Figure 4:
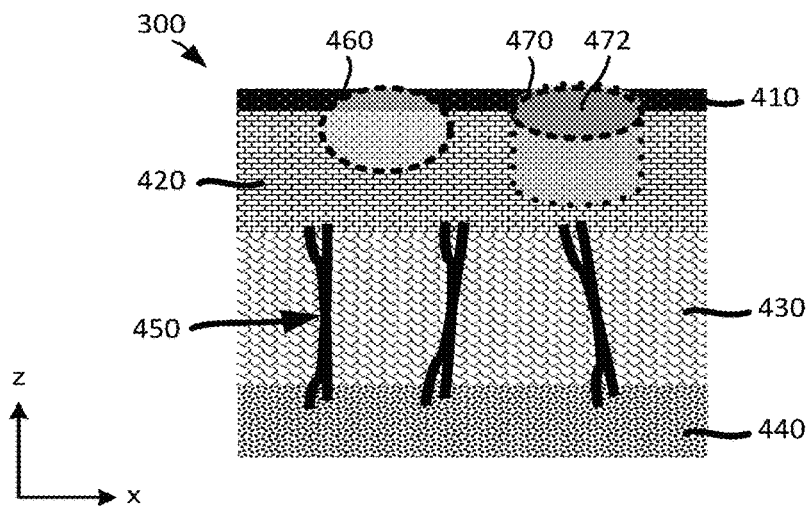
FIG. 4 is a drawing of a pair of therapy depth profiles within a set of layers of the skin due to the energy pulse according to an example.

The skin 300 can have a set of layers as shown in FIG. 4 according to an example. The set of layers of the skin 300 include an epidermis layer 410, a dermis layer 420, a fat cells layer 430, and a muscle layer 440 overlaid respectfully. The set of layers of the skin further include a set of septae 450 connecting the dermis layer 420 and the muscle layer 440. The set of layers of the skin may vary in thicknesses between individuals; however, the epidermis layer 410 typically has a thickness between 0.05-1.2 mm, the dermis layer 420 typically has a thickness between 1-4 mm, and the fat cells layer 430 typically has a thickness between 2-9 mm.

A pair of therapy depth profiles within the set of layers of the skin 300 due to the cooling effect of the dermal device 100 is shown in FIG. 4. A first therapy depth profile 460 shows a depth of the energy pulse limited to around 0-3 mm of the skin 300 without cooling the topical 460 or the skin 300 by the dermal device 100 providing RF energy therapy. A second therapy depth profile 470 shows the depth of the energy pulse extending beyond the first therapy depth profile 460 with cooling of the topical or the skin due to the dermal device 100 providing the energy pulse and simultaneous cooling. Further, a portion 472 of the second therapy depth profile 470 provides a cooler surface of the skin 300, which offsets heating occurring due to the energy pulse.

FIG. 5A-E

Figure 5A:
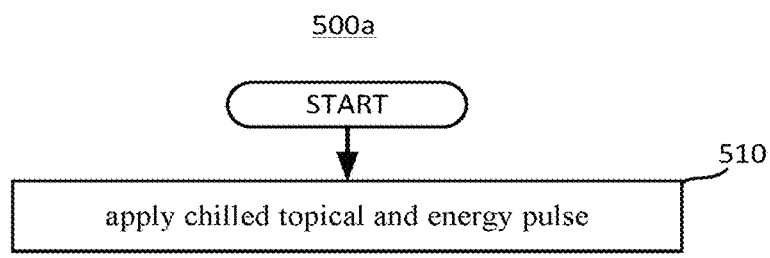
FIG. 5A shows a flow chart describing a method for conditioning a user's skin according to an example.

A method can be used for synchronization of one or more energy pulses and application of a set of topicals. FIG. 5A shows a flow chart describing a method 500a for conditioning a user's skin according to an example. At step 510, a dermal device 100 is configured to apply a chilled topical and an energy pulse to the skin. Examples of applying the chilled topical and the energy pulse to the skin include: applying a first topical and energy pulse (512) and optionally applying another topical and energy pulse (514). (See FIG. 5C)

Figure 5B:
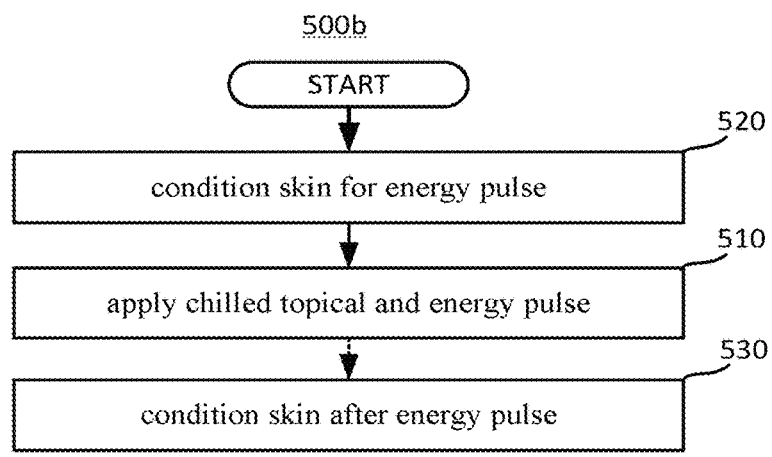
FIG. 5B shows a flow chart describing a method for conditioning a user's skin according to another example.

FIG. 5B shows a flow chart describing a method 500b for conditioning a user's skin according to another example. At step 520, a dermal device 100 is optionally configured to condition the skin for an energy pulse. Examples of conditioning the skin prior to the energy pulse include: applying a chilled topical to modify the skin temperature (522), applying an energy pulse to modify the skin impedance (524), and applying an energy pulse to modify blood flow in the skin (526). (See FIG. 5D)

Optionally, the method 500a or 500b can include a step 530 where the dermal device 100 is configured to condition the skin after the energy pulse. Examples of conditioning the skin after the energy pulse include: applying another topical (532). (See FIG. 5E)

FIGS. 6A-6B

Figure 6A:
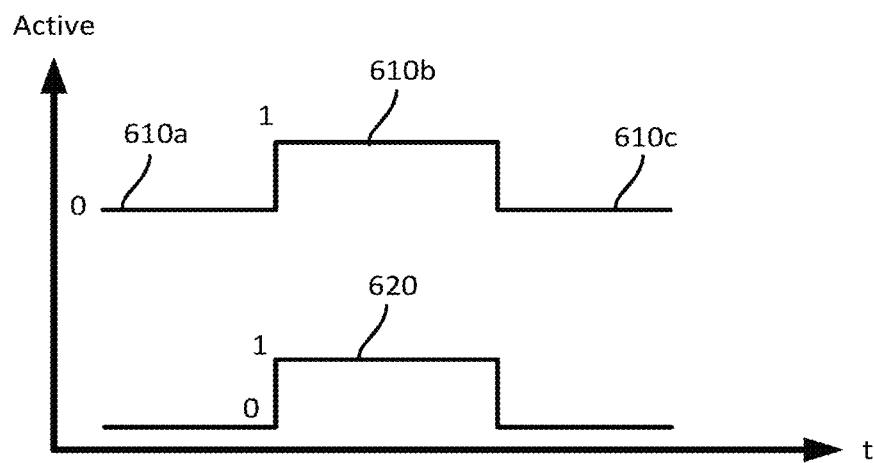
FIG. 6A shows a graph indicating synchronization of the RF energy therapy providing an energy pulse and application of a topical according to an example.
Figure 6B:
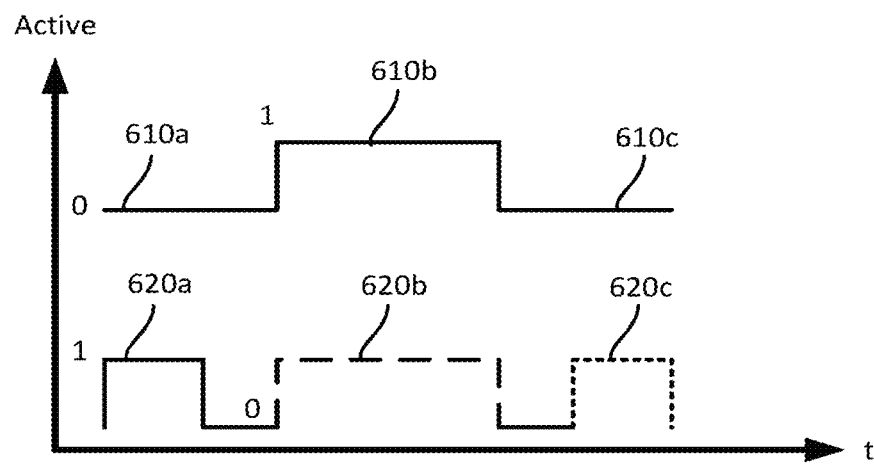
FIG. 6B shows a graph indicating synchronization of the RF energy therapy providing the energy pulse and application of a set of topicals according to an example.

FIG. 6A shows a graph indicating synchronization of an RF energy therapy providing an energy pulse 610a-610c and application of a topical 620 according to an example. FIG. 6B shows a graph indicating synchronization of an RF energy therapy providing an energy pulse 610a-610c and application of a set of topicals 620a-620c according to an example. A first topical 620a can be circulated prior to activation of the energy pulse (610a), a second topical 620b can be circulated during activation of the energy pulse (610b), and a third topical 620c can be circulated after activation of the energy pulse (610c). Obviously, numerous modifications and variations of the synchronization of the RF energy therapy and application of the set of topicals are possible.

Obviously, numerous modifications and variations of the present invention are possible in light of the above teachings. It is therefore to be understood that within the scope of the appended claims, the invention may be practiced otherwise than as specifically described herein.

The invention claimed is:

1. A dermal device for skincare therapy comprising:
a fluid circuit including a fluid pump and a reservoir; and
a dermal interface configured to contact a user's skin,
the dermal interface including at least one electrode and being configured to contact the user's skin and further including part of the fluid circuit having at least one perforation, the at least one electrode being supported by a portion of the fluid circuit that directly contacts the user's skin and that is adjacent to the at least one perforation,
wherein the at least one electrode is configured to deliver at least one energy pulse to the contacted skin,
wherein the reservoir is configured to hold at least one topical,
wherein the fluid pump is configured to pump the at least one topical through the fluid circuit and extrude the at least one topical through the dermal interface,
wherein the fluid circuit has a curved shape at a distal portion of the dermal device that supports the at least one perforation and the at least one electrode, and the at least one perforation and the at least one electrode are configured to be disposed adjacent to each other along a portion of the curved shape that is configured to face the user's skin.

2. The dermal device of claim 1, wherein the at least one perforation is a plurality of perforations that are configured to surround the at least one electrode interfacing the skin.

3. The dermal device of claim 1, wherein the at least one energy pulse applied to the skin is configured to reduce a skin impedance,
wherein the contacted skin is conditioned for the skincare therapy by a reduction in the skin impedance.

4. The dermal device of claim 1, wherein the at least one topical is chilled,
wherein the contacted skin is conditioned for the skincare therapy by a reduction in temperature.

5. The dermal device of claim 1, wherein the dermal interface is configured to be removable.

6. The dermal device of claim 1, including a power source to generate the at least one energy pulse.

7. A method for conditioning a user's skin, the method implemented by a dermal device for skincare therapy including a fluid circuit including a fluid pump and a reservoir, and a dermal interface configured to contact the user's skin, the dermal interface including at least one electrode and being configured to contact the user's skin and further including part of the fluid circuit having at least one perforation, the at least one electrode being supported by a portion of the fluid circuit that directly contacts the user's skin and that is adjacent to the at least one perforation, wherein the at least one electrode is configured to deliver at least one energy pulse to the contacted skin, wherein the reservoir is configured to hold at least one topical, wherein the fluid pump is configured to pump the at least one topical through the fluid circuit and extrude the at least one topical through the dermal interface, wherein the fluid circuit has a curved shape at a distal portion of the dermal device that supports the at least one perforation and the at least one electrode, and the at least one perforation and the at least one electrode are configured to be disposed adjacent to each other along a portion of the curved shape that is configured to face the user's skin, the method comprising:
chilling the at least one topical; and
applying the chilled at least one topical and the at least one energy pulse to the skin.

8. The method of claim 7, wherein applying the chilled at least one topical and the at least one energy pulse to the skin includes applying a first topical and an energy pulse, and applying another topical and another energy pulse.

9. The method of claim 7, further comprising:
conditioning the skin for the at least one energy pulse.

10. The method of claim 9, wherein conditioning the skin for the at least one energy pulse includes applying the chilled at least one topical configured to modify a temperature of the skin.

11. The method of claim 9, wherein conditioning the skin for the at least one energy pulse includes applying an energy pulse configured to modify an impedance of the skin.

12. The method of claim 9, wherein conditioning the skin for the at least one energy pulse includes applying an energy pulse configured to modify a blood flow in the skin.

13. The method of claim 7, further comprising:
conditioning the skin after the at least one energy pulse including applying another topical.

* * * * *